(12) United States Patent
Peake

(10) Patent No.: US 10,702,722 B2
(45) Date of Patent: Jul. 7, 2020

(54) SYSTEM AND METHOD FOR MONITORING PSA BED HEALTH

(71) Applicant: Carleton Life Support Systems, Inc., Davenport, IA (US)

(72) Inventor: Steven C. Peake, Dubuque, IA (US)

(73) Assignee: Cobham Mission Systems Davenport LSS Inc., Davenport, IA (US)

( * ) Notice: Subject to any disclaimer, the term of this patent is extended or adjusted under 35 U.S.C. 154(b) by 265 days.

(21) Appl. No.: 15/950,767

(22) Filed: Apr. 11, 2018

(65) Prior Publication Data

US 2018/0289992 A1 Oct. 11, 2018

Related U.S. Application Data

(60) Provisional application No. 62/484,205, filed on Apr. 11, 2017.

(51) Int. Cl.
| | |
|---|---|
| *B01D 53/047* | (2006.01) |
| *A61M 16/10* | (2006.01) |
| *A62B 7/14* | (2006.01) |
| *A62B 27/00* | (2006.01) |
| *B01D 53/04* | (2006.01) |

(52) U.S. Cl.
CPC ............ *A62B 27/00* (2013.01); *A61M 16/101* (2014.02); *B01D 53/047* (2013.01); *B01D 53/0454* (2013.01); *A61M 2016/1025* (2013.01); *A62B 7/14* (2013.01); *B01D 2256/12* (2013.01); *B01D 2257/102* (2013.01); *B01D 2259/402* (2013.01); *B01D 2259/4575* (2013.01)

(58) Field of Classification Search
CPC ........ A61M 16/101; A61M 2016/1025; A62B 27/00; A62B 7/14; B01D 53/0454; B01D 53/047; B01D 2256/12; B01D 2257/102; B01D 2259/402; B01D 2259/4575
USPC ............. 96/111, 117, 121; 95/130, 96, 8, 11
See application file for complete search history.

(56) References Cited

U.S. PATENT DOCUMENTS

| | | | |
|---|---|---|---|
| 5,004,485 A | 4/1991 | Lamlin et al. | |
| 5,071,453 A | 12/1991 | Hradek et al. | |
| 5,858,063 A | 1/1999 | Cao et al. | |
| 5,893,944 A * | 4/1999 | Dong | B01D 53/053 96/114 |
| 6,669,758 B1 | 12/2003 | Hart et al. | |
| 6,688,308 B1 * | 2/2004 | Phillips | A62B 27/00 128/204.22 |

(Continued)

FOREIGN PATENT DOCUMENTS

| | | |
|---|---|---|
| EP | 0250235 | 12/1987 |
| EP | 0760247 | 3/1997 |

(Continued)

*Primary Examiner* — Frank M Lawrence, Jr.
(74) *Attorney, Agent, or Firm* — Woods Oviatt Gilman LLP; Katherine H. McGuire, Esq.

(57) ABSTRACT

A system for monitoring the bed health of a molecular sieve bed within a pressure swing adsorption (PSA) system includes an oxygen sensor coupled to an outlet of the PSA system. The oxygen sensor measures an oxygen concentration of an output air produced by the molecular sieve bed. A controller is in communication with the oxygen sensor and records a series of oxygen concentrations over time. The controller is configured to determine bed health based upon the series of recorded oxygen concentrations.

5 Claims, 3 Drawing Sheets

(56) References Cited

U.S. PATENT DOCUMENTS

| | | | |
|---|---|---|---|
| 6,889,144 B2 | 5/2005 | Borkman et al. | |
| 7,152,494 B2 | 12/2006 | Peacey et al. | |
| 9,089,721 B1 * | 7/2015 | Horstman | A62B 7/14 |
| 2003/0167924 A1 * | 9/2003 | McCombs | B01D 53/0446 |
| | | | 96/121 |
| 2006/0062707 A1 | 3/2006 | Crome et al. | |
| 2011/0208466 A1 | 8/2011 | Quast | |
| 2015/0196245 A1 | 7/2015 | Peake | |
| 2017/0014774 A1 | 1/2017 | Daniello | |

FOREIGN PATENT DOCUMENTS

| | | |
|---|---|---|
| EP | 0860646 | 8/2007 |
| FR | 2880328 | 7/2006 |
| WO | 2004096111 | 11/2004 |

* cited by examiner

SYSTEM AND METHOD FOR MONITORING PSA BED HEALTH

CROSS REFERENCE TO RELATED APPLICATIONS

This Application claims the benefit of U.S. Provisional Application No. 62/484,205 filed Apr. 11, 2017, which is hereby incorporated by reference in its entirety.

FIELD OF THE INVENTION

The present invention generally relates to pressure swing adsorption systems, and more particularly to a system and method of monitoring the health of the molecular sieve beds used within a pressure swing adsorption system.

BACKGROUND OF THE INVENTION

Current Pressure Swing Absorption ("PSA") systems generally utilize molecular sieve material, such as zeolite, to separate incoming air from an air source, such as engine bleed air of an aircraft, by adsorbing nitrogen from the bleed air while allowing oxygen to pass therethrough. The separated oxygen may then be ultimately directed to specific areas (e.g., cockpit, cabin) and personnel (e.g., pilot, crew, passengers) aboard the aircraft so as to provide a breathable gas. The adsorbed nitrogen may be periodically purged from the zeolite under reduced pressure (e.g., at ambient pressure) by using pressure swing techniques in a known manner. The purged nitrogen is then either dumped overboard or used for other purposes, such as inerting the fuel tank ullage of the aircraft.

However, the material used in the molecular sieve beds degrades over time, especially when exposed to moisture or contaminants in the supply air. One problem encountered in the art is determining how much the sieve has degraded so as to allow proper and timely maintenance actions to recharge or replace a bed unit. This problem is especially true in regard to aircraft On Board Oxygen Systems ("OBOGS"). For OBOGS systems, it has been necessary to provide a known demand on the PSA oxygen concentrator, then measure the oxygen concentration produced and compare it to desired oxygen concentration levels. This approach, however, leads to several problems. For instance, it is difficult to do this on the aircraft without special actions such as valves controlling output flow rate and controlled inlet pressure conditions. These additional activities do not fit well with routine maintenance monitoring and add cost and complexity to operation of the aircraft. They also do not provide the necessary timely information about the health of the sieve material for each flight.

Thus, what is needed is a system and method for monitoring the health of the molecular sieve beds within a PSA system which does not require special actions or cumbersome flow control protocols.

SUMMARY OF THE INVENTION

In view of the above and in accordance with an aspect of the present invention, the present invention is generally directed to a system for monitoring the bed health of a molecular sieve bed within a pressure swing adsorption (PSA) system includes an oxygen sensor coupled to an outlet of the PSA system. The oxygen sensor measures an oxygen concentration of an output air produced by the molecular sieve bed. A controller is in communication with the oxygen sensor and records a series of oxygen concentrations over time. The controller is configured to determine bed health based upon the series of recorded oxygen concentrations.

In a further aspect of the invention, a method of monitoring the bed health of a molecular sieve bed within a pressure swing adsorption (PSA) system of an on-board oxygen generating system (OBOGS) includes a) powering the OBOGS; b) passing feed air into a first molecular sieve bed of the PSA system to produce an output gas; c) measuring an oxygen concentration of the output gas; d) cycling the PSA system to produce an oxygen-enriched output gas; e) measure the oxygen concentration of the oxygen-enriched output gas at regular time intervals until the oxygen concentration reaches a predetermined level; f) determining a length of time for the PSA system to reach the predetermined oxygen concentration; g) compare the length of time against a performance curve; and h) determine the bed health as a function of step g).

BRIEF DESCRIPTION OF THE DRAWINGS

The invention will further be described, by way of example, with reference to the accompanying drawings.

DETAILED DESCRIPTION

Figure 1:
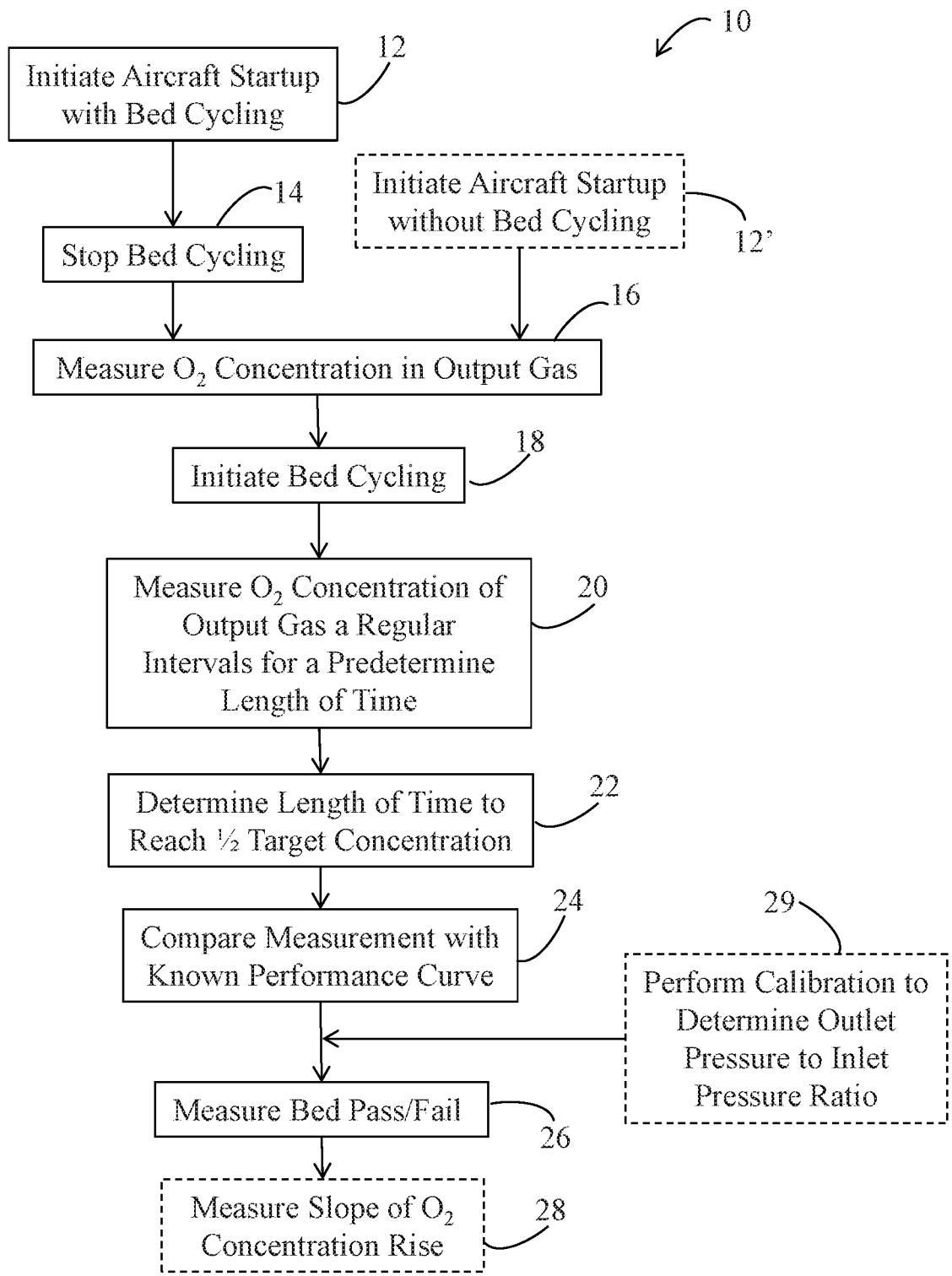
FIG. 1 is a flowchart of an exemplary method for monitoring the health of a molecular sieve bed within a PSA system in accordance with an aspect of the present invention.
Figure 2:
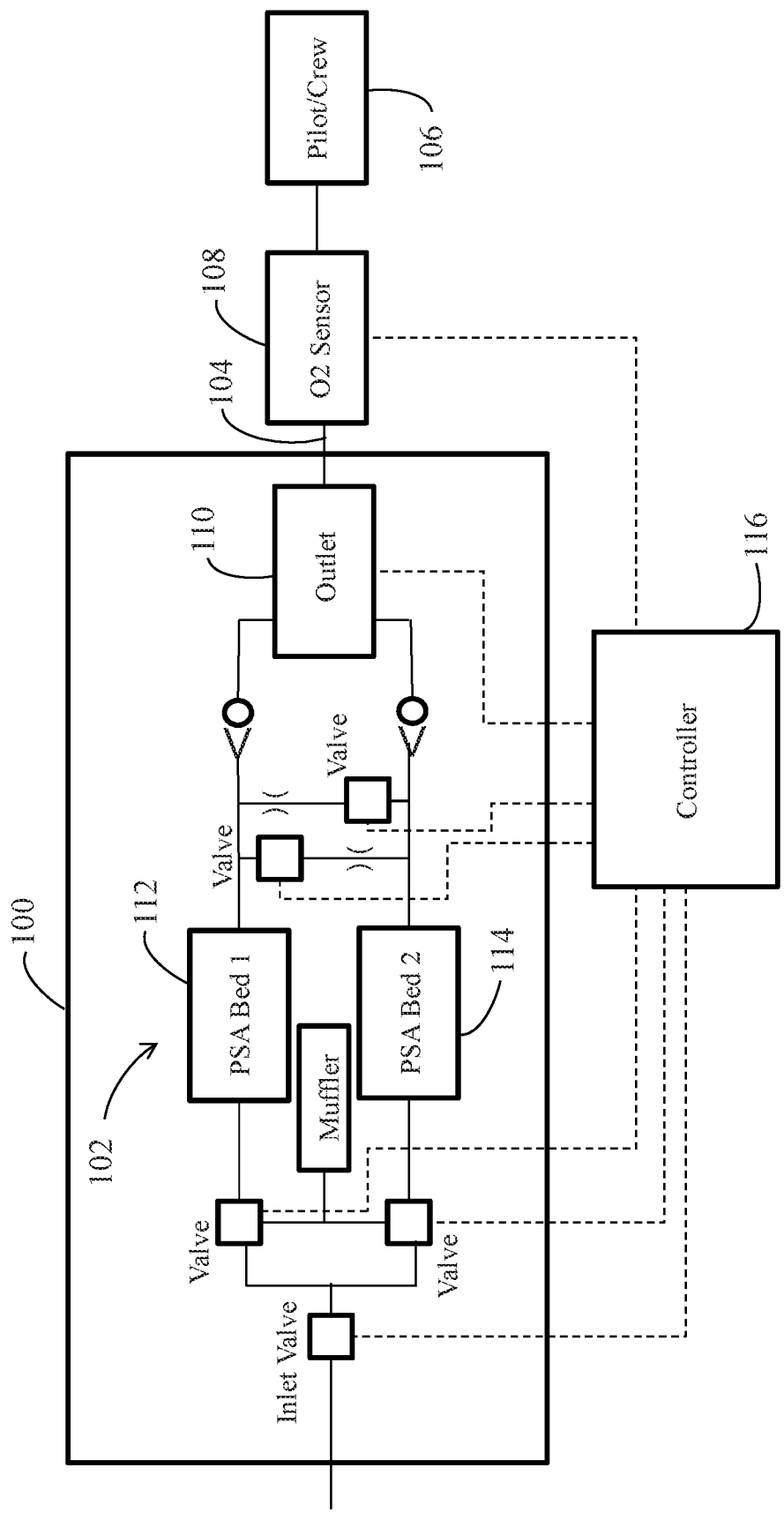
FIG. 2 is a schematic of an exemplary system for monitoring the health of a molecular sieve bed within a PSA system in accordance with an aspect of the present invention.

With reference to FIG. 1, in accordance with an aspect of the present invention, a method 10 for monitoring the health of a Pressure Swing Absorption (PSA) bed generally utilizes the inherent recovery time of the PSA bed to concentrate the desired gas to measure the health or amount of degradation that has occurred within the bed. When used with aircraft, and more particularly military aircraft, method 10 may be implemented during the initial power up sequence of the PSA system prior to each flight operation. It should be noted that method 10 may also be implemented at other times, such as during routine maintenance, to decrease the test time and complexity of bed health testing. However, employment of method 10 during power up of the aircraft is especially important to aircraft operations since it provides an assessment of the PSA performance prior to any flight operations. Continuing the aircraft example and as shown in FIG. 2, an On Board Oxygen Generating System (OBOGS) 100 with a PSA system 102 is configured to generate an output gas 104 having a high concentration of oxygen gas for ultimate delivery to pilots and crew 106, particularly when the aircraft is at high altitude. During the Power up Built in Test (PBIT) of the aircraft, the OBOGS 100 may go through a warm-up period as part of aircraft startup and checkout prior to any flight. As a result, method 10 may be employed during the PBIT or other initiation sequence and may provide a reading of the health of the PSA bed unit while the aircraft is on the ground. Proper decisions can then be made regarding risk of a fault of the OBOGS 100 and/or PSA system 102 during the flight or mission of the aircraft.

Exemplary method 10 may be used with an OBOGS 100 to monitor (such as via oxygen sensor 108) the oxygen concentration of output gas 104 exiting OBOGS outlet 110 in real time while the operating conditions of the PSA are varied. It should be noted that the following discussion will be directed to a PSA system employing two beds 112, 114. In this instance, one bed is typically under pressure to produce the desired product gas (oxygen, O2) while the other bed is undergoing desorption of adsorbed gas (i.e., nitrogen, N2) at lower (i.e. ambient) pressure. However, one skilled in the art should recognize that method 10 may be used for a 3 or more bed system with appropriate adaptions to account for the additional beds. It should be further noted that, for aircraft applications, it is important that method 10 be inhibited when the aircraft the crew is reliant on the oxygen concentration for breathing, such as when at altitude. Thus, method 10 may be disabled when the aircraft is not on the ground.

As shown in FIG. 1, method 10 may initiate upon aircraft startup (step 12) with controller 116 instructing OBOGS 100 to cycle the two-beds 112, 114 of PSA unit 102 at its typical duty cycle, for instance every 4-8 seconds, with different bed configurations potentially having significantly different duty cycles. Aircraft startup may take several minutes (e.g., 2 to 4 minutes) such that, during the later portion of the OBOGS warm-up period, such as minutes 3 to 4 post startup, the cycling of the PSA beds is stopped such that airs passes over one bed (e.g., bed 112) for a period longer than the typical ½ cycle, for instance, 2 to 4 seconds (step 14). The duration of step 14 may be around 5-6 times the length of a bed half cycle, for instance 10 to 30 second. During step 14, the active sites on the PSA bed (e.g., bed 112) receiving the feed air become saturated (such as with $N_2$) such that the molecular sieve material no longer enriches the output gas 104. It should be noted that the above times are merely exemplary and that the half cycle of the beds is typically dependent on the configuration of the PSA and can vary accordingly. Additionally, the duration of step 14 may vary depending on the accuracy requirement for measurement, the time allowed, as well as the configuration of the bed. As a result of sieve saturation, the O2 concentration within the output gas 104 will drop to near ambient (21%). Sieve saturation and O2 concentrations may be verified by measurement using O2 sensor 108 at step 16. If the measured O2 concentration is not within a tolerance band, such as 21%+/−3% O2, either the O2 sensor 108 is faulty or the OBOGS 100 and/or PSA system 102 has another operational fault. Aircraft startup may then be stopped for diagnosis and maintenance of the affected systems/components. It should also be noted that the tolerance of the O2 measurement in step 16 may be dependent on the necessary accuracy of the readings for specific applications.

At step 18, bed cycling is then re-initiated to thereby allow concentration of O2 (removal of N2 through adsorption to the molecular sieve material) to start as normal. At step 20, the O2 concentration of the output product gas is measured at regular intervals, such as once every second. In accordance with an aspect of the present invention, the time required to achieve approximately ½ the target concentration of the OBOGS is measured at step 22. Continuing the aircraft example, an OBOGS system has a target, or maximum, O2 concentration of around 93% O2. Thus, at step 20 the percent O2 is measured regularly until the O2 concentration reaches a user defined level, such 50% O2 at step 22. The time measured at step 22 may then be compared to a predetermined, known performance curve for the OBOGS/PSA system (see example below, FIG. 3) stored within controller 116 or an off-board diagnostic unit to determine the condition or 'health' of the PSA sieve beds (step 24).

Figure 3:
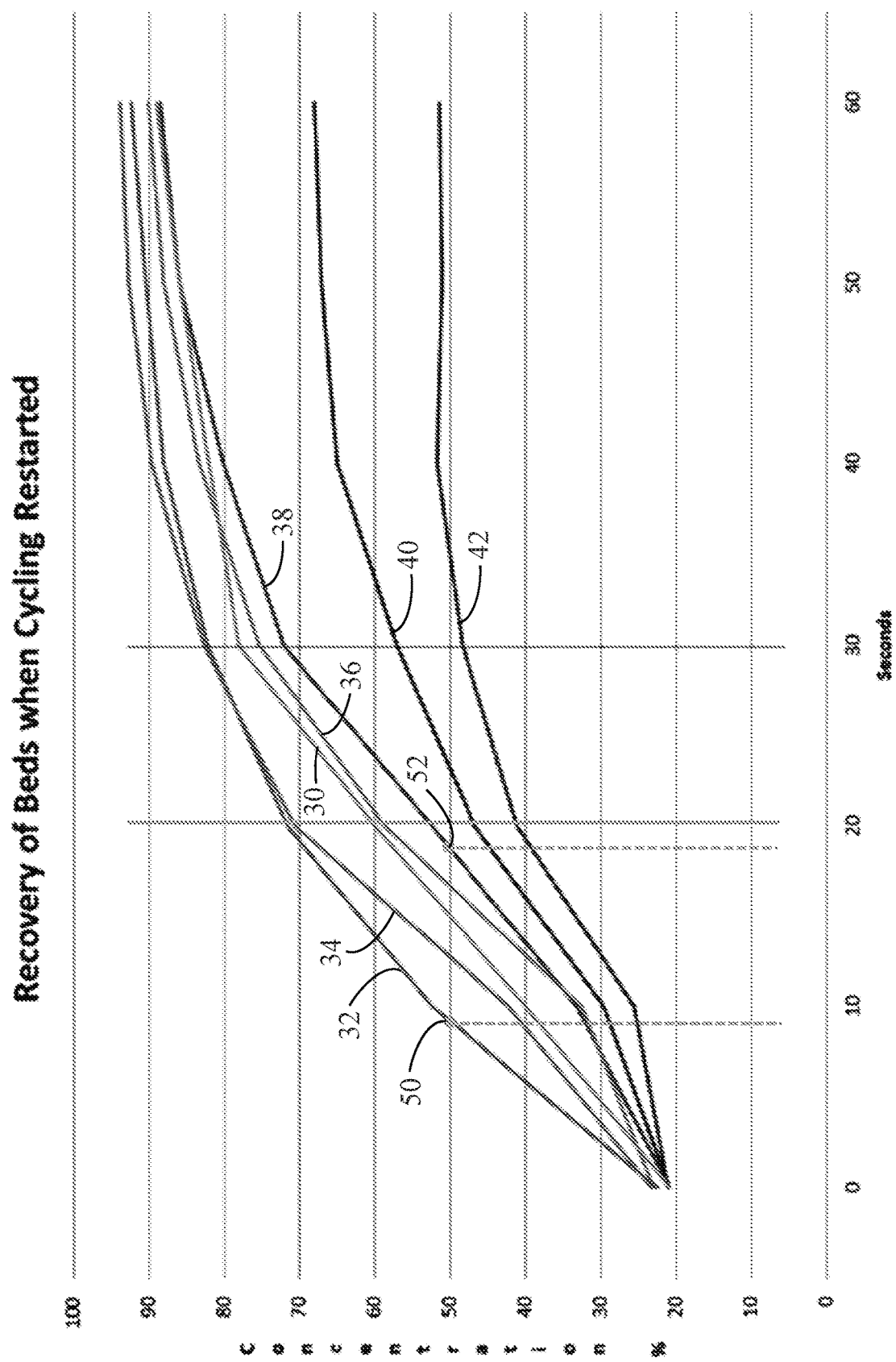
FIG. 3 is a plot of a series of PSA molecular sieve bed units showing percent oxygen concentration as a function of time.

As shown in FIG. 3, computer modeling has been used to verify the curve shape for recovery of the O2 concentration of a PSA sieve bed, see curve 30. As can be seen in FIG. 3, modeling curve 30 may be compared to empirical measurements 32, 34, 36 for the recovery of the O2 concentration of various PSA sieve beds (curve 32 was generated by a new PSA system after 10 liters of O2 production; curve 32 was generated by a new PSA system having 0 liters of O2 production; and curve 34 was generated by a PSA system that has been regenerated to near-new condition). As a result, modeling curve 30 correlates well with empirical curves 32-36, thereby validating method 10 as a diagnostic test for PBOGS/PSA system performance.

With continued reference to FIG. 3, it can be seen that as the PSA sieve material degrades, the shape of the recovery curve changes. By way of example, as can be seen by curve 38, a bed system degraded to the point where it still produces enriched oxygen concentration, but at a concentration approximately 70% as opposed to a new system producing 93%, the time to reach 50% concentration is approximately twice as long as a new unit (compare point 50 on curve 32 at approximately 9 seconds to point 52 on curve 38 at approximately 18 seconds). Accordingly, measuring the time it requires a saturated PSA sieve bed to generate 50% O2 may be used to assess bed health in less than one minute.

With continued reference to FIG. 3, method 10 may further include a pass fail measure step 26 for PSA bed health. In one aspect of the present invention, at step 26 the % O2 may be measured at a predetermined time, such as 20 seconds following initiating of step 18. If the measured % O2 is greater than 50%, method 10 may indicate that the PSA system is acceptable and flight operations may be conducted. However, if the measures % O2 is below 50% at 20 seconds, another measurement is taken at a second predetermine time, such as 30 seconds after initiation of step 18. If the second % O2 measured is greater than 50%, method 10 may indicate that OBOGS 100/PSA system 102 may be acceptable for flight operations but maintenance will soon be required (see e.g., curve 40). However, should the measured % O2 remain below 50%, method 10 may indicate a PSA system 102 failure and that flight operations should be suspended until the OBOGS 100/PSA system 102 is properly maintained or repaired (see e.g., curve 42).

It should be understood by those skilled in the art that the above times and concentrations are exemplary and non-limiting. That is, method 10 may have the OBOGS/PSA system run to levels higher than 50% of target test point for assessment of bed health. Alternatively, the shape of the recovery curve from 21% to a higher point, such as 70% or 90% may be used to assess the health of the bed.

In accordance with another aspect of the present invention, the PSA system is not cycled upon startup of the aircraft systems. Rather, steps 12 and 14 are omitted and method 10 begins at step 12' where air is passed through a single bed (e.g., bed 112) beginning with aircraft systems power up. Not cycling the PSA beds 112, 114 may allow a 21% O2 air stream to be measured at oxygen sensor 108 more quickly. Thus, once 21% O2 is measured at step 16, the remaining steps 18 through 29 of method 10 may proceed unchanged.

In still another aspect of the present invention, method 10 may include an additional or alternative step 28 wherein the slope of the oxygen concentration rise is calculated. By way of example, the maximum rate of change or maximum slope of the increase in % O2 may be indicative of the bed health and reduces sensitivity to other time variables within the system. For instance, and without limitation thereto, the slope may be calculated over 5 or 10 second periods beginning at step 18. The highest slope during a test period becomes the measurement of health, where the slope is reported as a bed health indication, either in % degradation or simply a slope or other number calculated. The slope reading for each startup is recorded and becomes a history of the trend for the health of the beds. There can also be a minimum slope, where if the beds fall below this slope, a warning is provided to the aircraft.

Thus, method 10 may report a relative degradation reading after each startup. For example, bed health may be reported as a percent of useful life consumed, or life remaining, in order to improve the predictability of preventative maintenance on bed refurbishment or replacement.

It should be noted that while outlet flow of the system does have some effect on the readings, it is not required to control the outlet or 'product' flow during method 10. Nevertheless, control of the product flow can be included to provide a higher degree of accuracy of the measurement of bed health. Also, for very high outlet flow rates which significantly reduce the capability of the system to concentrate oxygen to a high level, such as an open flow through a mask, additional steps may be required to restrict that outlet flow during bed health testing method 10. Still further, it is not required, but may be desirable, to control which bed within the system is exposed to a longer flow of ambient air for the first portion of method 10. This may prevent one bed from degrading more quickly than another in conditions where there is a high amount of contamination, such as moisture in the air supply stream. Method 10 may also include a calibration step 29 where the outlet pressure to inlet pressure ratio may be used to adjust the pass/fail threshold values. Temperature correction may also be used in this calibration.

Although the invention has been described with reference to preferred embodiments thereof, it is understood that various modifications may be made thereto without departing from the full spirit and scope of the invention as defined by the claims which follow.

What is claimed is:

1. A method of monitoring the bed health of a molecular sieve bed within a pressure swing adsorption (PSA) system of an on-board oxygen generating system (OBOGS), the method comprising:
   a) powering the OBOGS;
   b) passing feed air into a first molecular sieve bed of the PSA system to produce an output gas;
   c) measuring an oxygen concentration of the output gas;
   d) cycling the PSA system to produce an oxygen-enriched output gas;
   e) measuring the oxygen concentration of the oxygen-enriched output gas at regular time intervals until the oxygen concentration reaches a predetermined level;
   f) determining a length of time for the output gas to reach the predetermined oxygen concentration;
   g) comparing the length of time against a performance curve; and
   h) determining the bed health of the first molecular sieve bed as a function of step g).

2. The method of claim 1, further comprising:
   i) communicating the determined bed health, wherein the communication comprises one of:
      i) the first molecular sieve bed is fully operational; or
      ii) the first molecular sieve bed is operational but will require maintenance; or
      iii) the first molecular sieve bed is non-operational and requires immediate maintenance.

3. The method of claim 2, wherein the communication further includes an anticipated period of time until maintenance will be required.

4. The method of claim 2, wherein the communication further includes a measurement of a length of time since the last maintenance of the first molecular sieve bed.

5. A method of monitoring the bed health of a molecular sieve bed within a pressure swing adsorption (PSA) system of an on-board oxygen generating system (OBOGS), the method comprising:
   a) powering the OBOGS;
   b) passing feed air into the OBOGS;
   c) cycling the feed air between a first molecular sieve bed and a second molecular sieve bed, wherein one of the first or second molecular sieve beds is receiving the feed air at high pressure while the other of the first or second molecular sieve beds is at ambient pressure;
   d) stopping the cycling of the feed air;
   e) passing feed air into the first molecular sieve bed of the PSA system until an output gas has an oxygen concentration equal to the oxygen concentration of ambient air;
   f) confirming the oxygen concentration of the output gas;
   g) restarting cycling of the feed air between the first molecular sieve bed and the second molecular sieve bed to produce an oxygen-enriched output gas having an enriched oxygen concentration;
   h) measuring the enriched oxygen concentration of the oxygen-enriched output gas at regular time intervals until the enriched oxygen concentration reaches a predetermined level;
   i) determining a length of time for the output gas to reach the predetermined oxygen concentration;
   j) comparing the length of time against a performance curve; and
   k) determining the bed health of the first molecular sieve bed as a function of step j).

\* \* \* \* \*